United States Patent
Schwartz et al.

[11] Patent Number: 5,805,768
[45] Date of Patent: Sep. 8, 1998

[54] AROMA THERAPY DIFFUSER

[75] Inventors: Gary Schwartz, Van Nuys, Calif.;
Caleb Chung, Boise, Id.

[73] Assignee: Bunny Moon Enterprises, Van Nuys, Calif.

[21] Appl. No.: 676,823

[22] Filed: Jul. 8, 1996

[51] Int. Cl.[6] .................................................. F24F 6/00
[52] U.S. Cl. .................................. 392/390; 261/DIG. 65
[58] Field of Search .................................... 392/386, 390, 392/403; 219/214, 544; 222/146.1, 146.2, 146.3, 146.4; 261/DIG. 65, DIG. 70, DIG. 71; 338/275

[56] References Cited

U.S. PATENT DOCUMENTS

| | | | |
|---|---|---|---|
| 2,614,820 | 10/1952 | Boydjeff | 261/DIG. 65 |
| 3,319,210 | 5/1967 | Sandone, Jr. et al. | 338/275 |
| 4,588,874 | 5/1986 | Napierski | 392/390 |
| 5,023,020 | 6/1991 | Machida et al. | 261/DIG. 65 |
| 5,133,042 | 7/1992 | Pelonis | 392/390 |
| 5,167,877 | 12/1992 | Pai | 261/DIG. 65 |
| 5,220,636 | 6/1993 | Chang | 392/390 |
| 5,565,148 | 10/1996 | Pendergrass, Jr. | 261/DIG. 65 |

Primary Examiner—Geoffrey S. Evans
Assistant Examiner—Sam Paik

[57] ABSTRACT

An apparatus is provided for diffusing aroma therapy oils which allows the user to pre-select a variety of aromas to be introduced at predetermined time intervals so that different moods or state of minds may be created. The apparatus includes a tray having a plurality of receptacles for various aromatic materials, and a heating means for heating a pre-selected receptacle, and thus aromatic material. The apparatus also includes a motor driven timer, that rotates the tray, so that the plurality of receptacles containing different aromatic materials are exposed to the heating means at a predetermined time period. The apparatus further includes a lid with a hole that exposes the pre-selected receptacle and aromatic material when the receptacle and aromatic material are exposed to the heating means. The aroma released from the heated aromatic material emanates into the environment through the hole. The remaining receptacles, which are out of close proximity to the heating means, are sealed to avoid the evaporation of the aromatic materials.

9 Claims, 5 Drawing Sheets

AROMA THERAPY DIFFUSER

BACKGROUND OF THE INVENTION

1. Field of the Invention

The present invention relates generally to apparatuses for diffusing aromas into the environment.

2. Description of Related Art

Aroma therapy involves the use of oils or essences to create a state of mind or mood. The oils, often called essential oils, give off aromas, or essences. Different aromas or essences have been attributed to affecting and creating particular moods. For example, the aroma of lavender relaxes tension and alleviates stress; the aromas of mint and lemon are considered stimulants. An individual thus selects a particular aroma to introduce into the environment, depending on the desired mood or state of mind desired. It has been found that heating the oils increases the potency of the aromas.

There are many different methods and apparatuses for introducing aromas into the environment. Conventional methods include heating the essential oils by candle or an electric source, or burning candles scented with the essential oils. A considerable drawback of these methods and apparatuses is that these apparatuses allow the individual to introduce a single aroma at a time; the individual must change the oil or candle whenever a different mood is desired.

There have been some attempts to develop aroma delivering apparatuses that allow an individual to introduce a selection of different aromas into the environment. For example, U.S. Pat. No. 5,023,020 issued to Hiroji Machida et al. discloses and claims an apparatus for supplying various aromas into a zone that includes a plurality of reservoirs for aromatic materials, a controller for selecting a desired aroma, and a ventilator for supplying the air containing the aroma.

While this apparatus allows an individual to pre-select a variety of aromas to be introduced into the environment at a given predetermined time, the apparatus relies upon ventilating air to introduce the selected aroma. This is not the most convenient method for introducing the aroma into the environment when the aroma is not part of a ventilating system. Further, while some aromatic materials diffuse through ventilation, a number of aromatic materials, such as rosemary oil, vetiver, cedarwood, cinnamon, anise sandalwood oil do not release effective levels of aroma unless heated. Moreover, many aromatic materials are costly, and the apparatus has no means for preventing the evaporation of the aromatic materials not in use, which decreases the efficiency of the system.

Therefore, there is a need for a diffusing apparatus that effectively and efficiently introduces desired aromas into the environment or a room at preselected intervals without the need for a ventilating system.

SUMMARY OF THE INVENTION

The present invention resides in an efficient and effective aroma therapy diffuser which offers the user the ability to pre-select a variety of different aromas to be introduced into an environment at pre-selected time periods. Briefly, and in general terms, the diffuser includes a tray with a plurality of receptacles for receiving aromatic materials arranged along the periphery of the tray and a means for heating a selected receptacle, and thus aromatic material contained therein. The apparatus also includes a timer and a means for rotating the receptacles about the heating means as desired, so as to expose to the environment a selected receptacle containing an aromatic material for a pre-selected time period. The apparatus further includes a lid with an opening which exposes the selected receptacle and aromatic material so that the aroma released by the heated aromatic material emanates into the environment. The remaining aromatic materials which are not exposed to the heating means are sealed to prevent evaporation.

In another embodiment of the invention, the tray is decorated with a clock face. The rotating means rotates the tray through a 24 hour cycle so that the invention operates as a normal time clock as well as a diffuser.

It will be appreciated from the forgoing that the present invention represents an advance in the field of aroma therapy diffusers. In particular, the invention provides an efficient and effective diffuser which allows an individual to pre-select aromas to be released into the environment at predetermined time periods so as to create different moods and state of minds as desired. Because an individual can pre-select a variety of aromas to be introduced into the environment at various time throughout the day, the apparatus requires less monitoring than other diffusers. The fact that the aromatic materials are heated to a temperature sufficient to enhance diffusion of the aromatic material increases the effectiveness of the aromatic materials, and thus, the effectiveness of the diffuser. The flexibility and efficiency offered by this invention is further enhanced by the fact that the invention includes a seal for the unexposed aromatic materials to prevent evaporation of such when not in use. Moreover, because the diffuser operates without a ventilation system, it can be scaled down to a stand alone size, without impacting its effectiveness. The flexibility of the diffuser is further enforced by the fact that it can be operated by batteries, may be, therefore, portable and not bound to a specific area as those which require a ventilation system. Thus the diffuser requires less attention and maintenance than others and uses less aromatic materials.

Other aspects and advantages of the invention will become apparent from the following more detailed description, taken in conjunction with the accompanying drawings.

DETAILED DESCRIPTION

Figure 1:
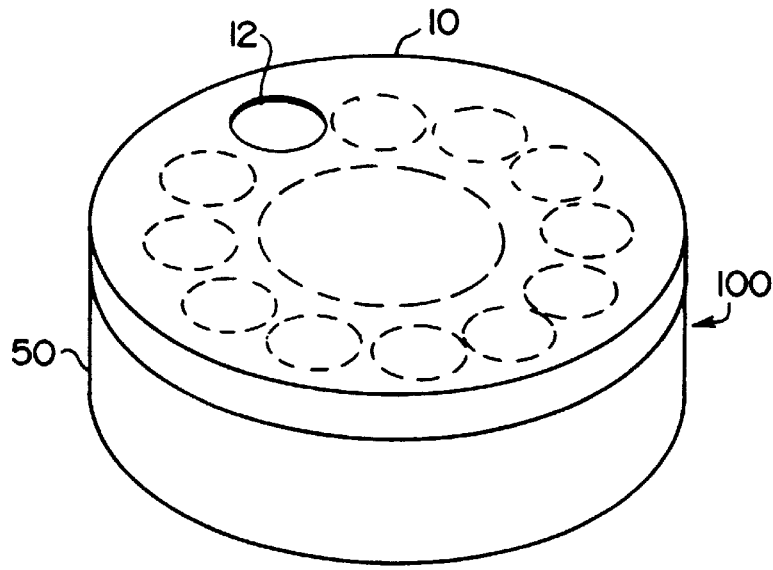
FIG. 1 is a perspective view of an aroma therapy diffuser in accordance with the present invention.
Figure 2:
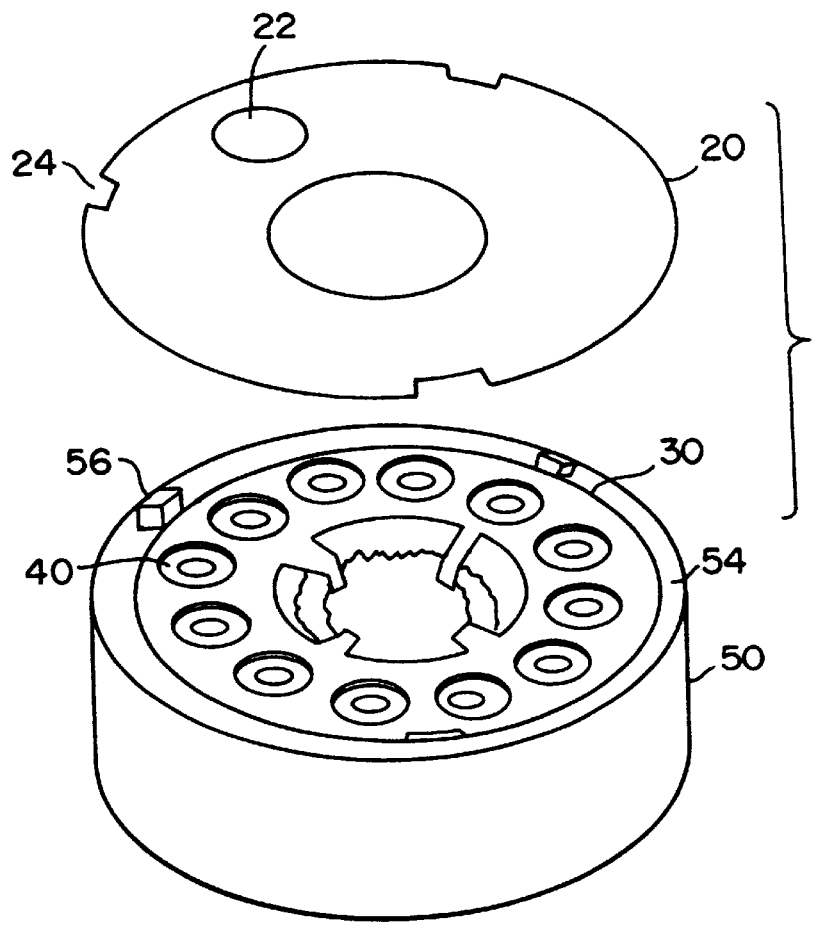
FIG. 2 is a perspective view of the invention, without the lid, showing the placement of the sealing means and tray within the housing.

As shown in FIG. 1, an exemplary aroma therapy diffusing apparatus 100 generally includes a lid 10 having a hole 12 through which the aromas emanate, and a housing 50 upon which lid 10 rests. As shown in FIG. 2, tray 30 resides between lid 10 and housing 50. Tray 30 has a plurality of receptacles 40 into which aromatic material is deposited, receptacles 40 being disposed about the periphery of tray 30. It is preferred, as illustrated in FIG. 3, that receptacles 40 be removable from tray 30, as it is easier to clean the individual receptacles as needed, rather than the entire tray.

Figure 3:
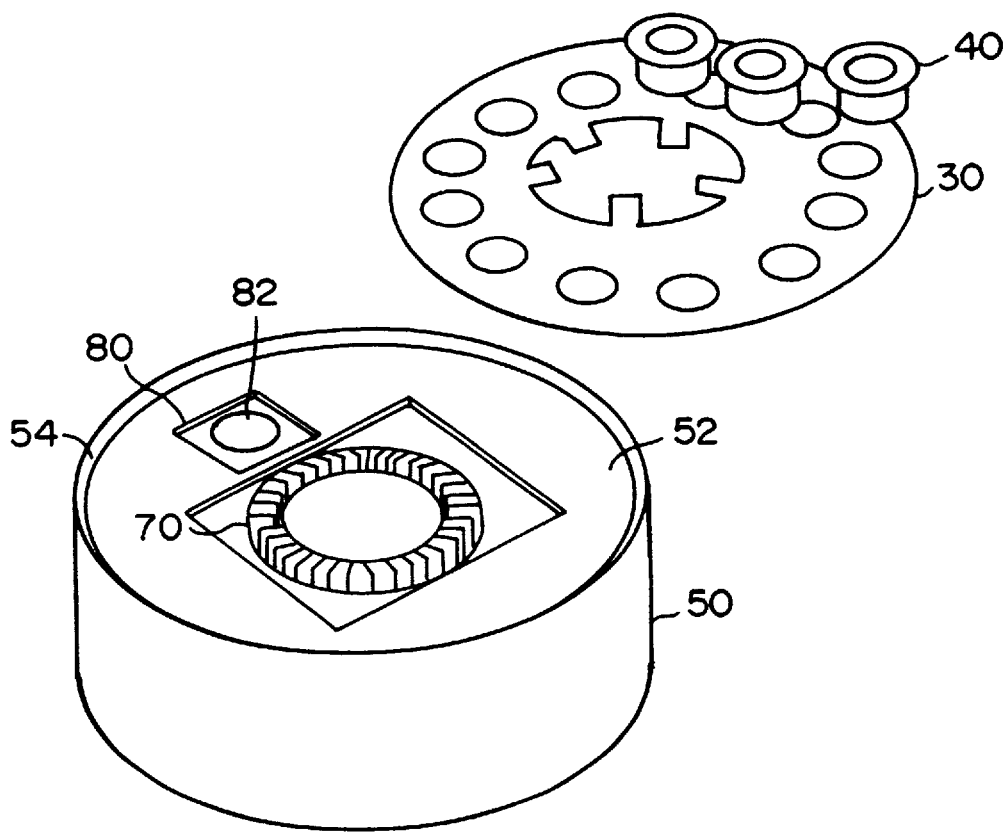
FIG. 3 is a perspective view of the invention showing the components of the tray and removable receptacles, and the heating element and rotating means.
Figure 4:
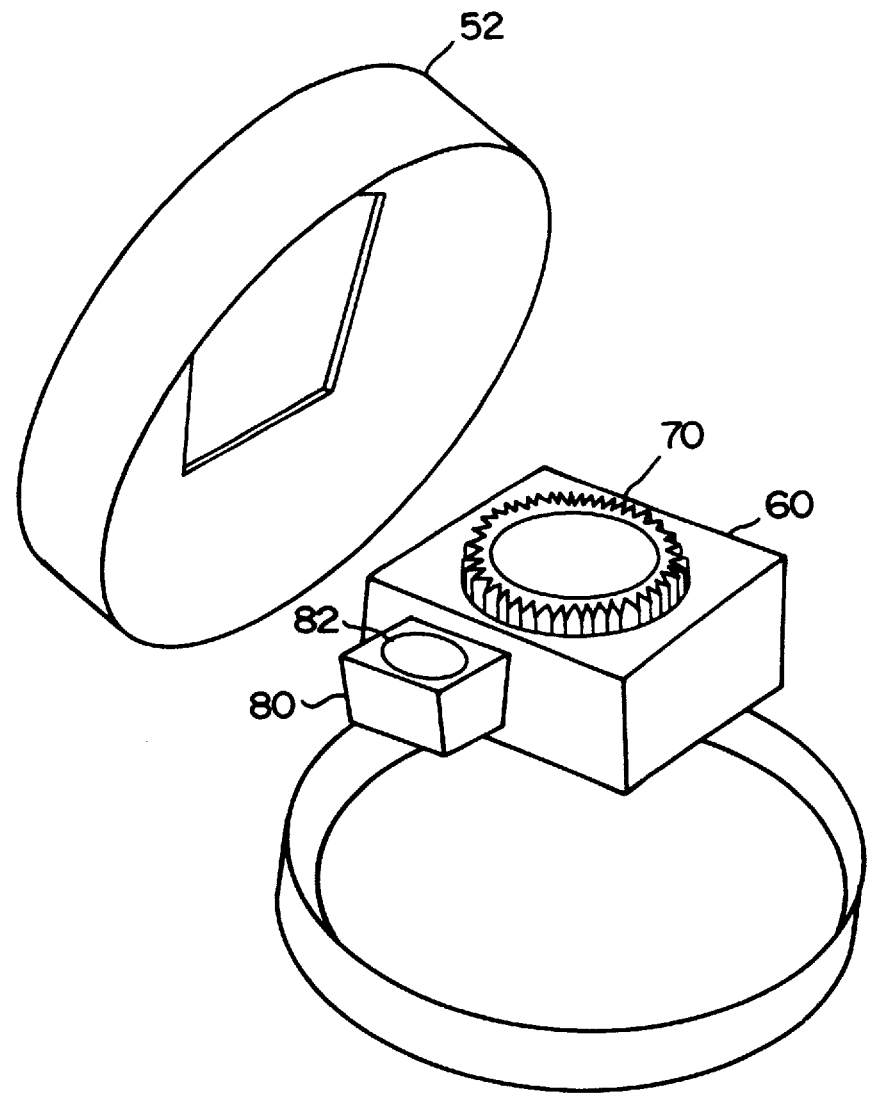
FIG. 4 is an elevated side view showing the components of the placement of the timer and heating elements within the housing.

As further illustrated in FIGS. 3 and 4, housing 50 includes a surface 52 and side surfaces 54. Tray 30 is detachably coupled to surface 52. A timer 60 is disposed within housing 50, and includes a rotating means 70, which engages tray 30, causing the tray to rotate. Housing 50 further includes a heating component 80 disposed within surface 52 of the housing. The heating component 80 has an activated and deactivated state. As tray 30 rotates, receptacles come into close proximity to heating component 80. Heating component 80 is coupled to timer 60.

Figure 7:
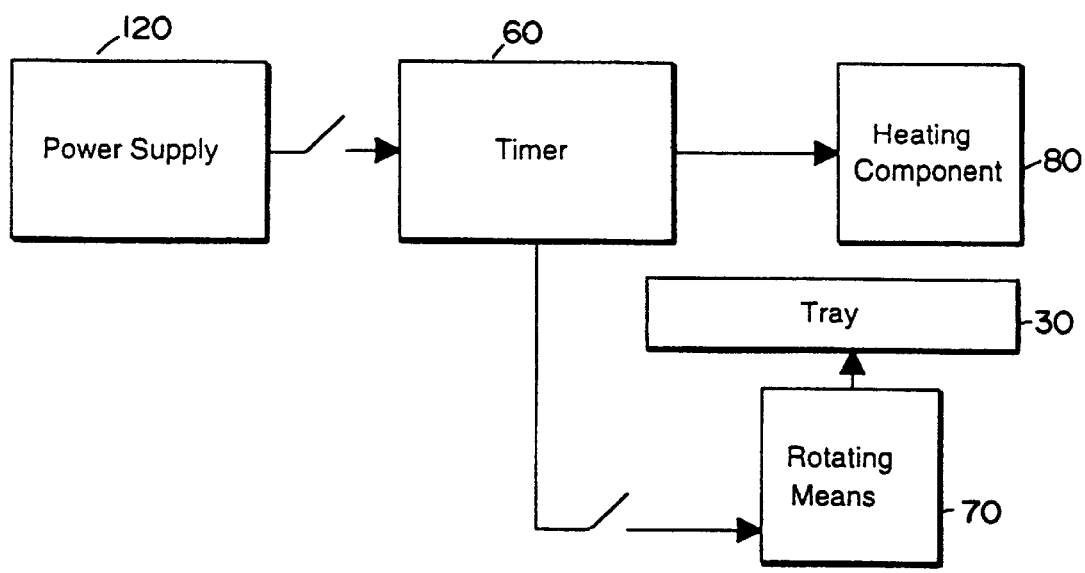
FIG. 7 is a block diagram illustrating an embodiment of the invention.

Timer 60 can be programmed to activate or deactivate heating component 80. As shown in FIG. 7, timer 60 is activated by power supply 120. When in use, timer 60 engages rotating means 70, which in turn rotates tray 30. Various aromatic materials are deposited into the receptacles of tray 30. As tray 30 rotates, the receptacles pass over heating component 80. If the heating component is activated by timer 60, the aromatic material contained within the receptacle in close proximity to the heating component at that time is heated to a sufficient temperature so that aroma is diffused. Hole 12 of lid 10 is in alignment with the heating component, so that the aroma is transmitted into the environment or room. Timer 60 can also be programmed to disengage rotating means 70, so that the tray remains stationary for a preselected time period, and a preselected receptacle remains in close proximity to heating component 80, to be heated as programmed by timer 60.

Figure 5:
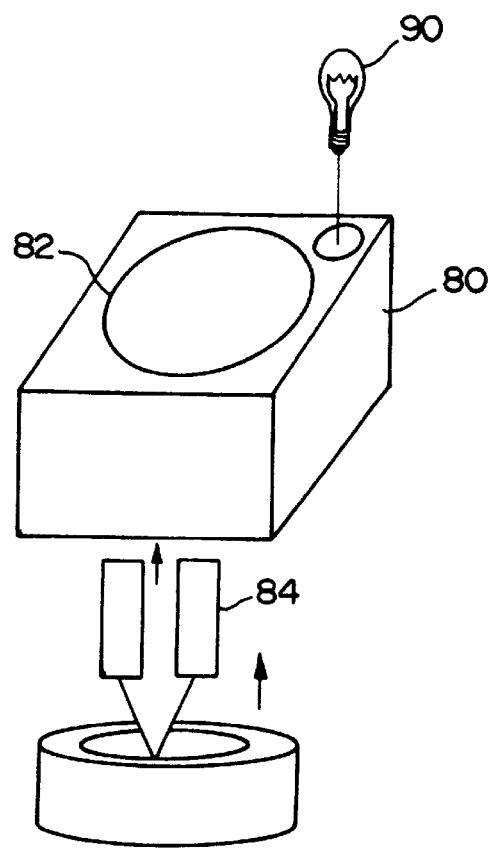
FIG. 5 is a side view of the components of the heating elements.
Figure 6:
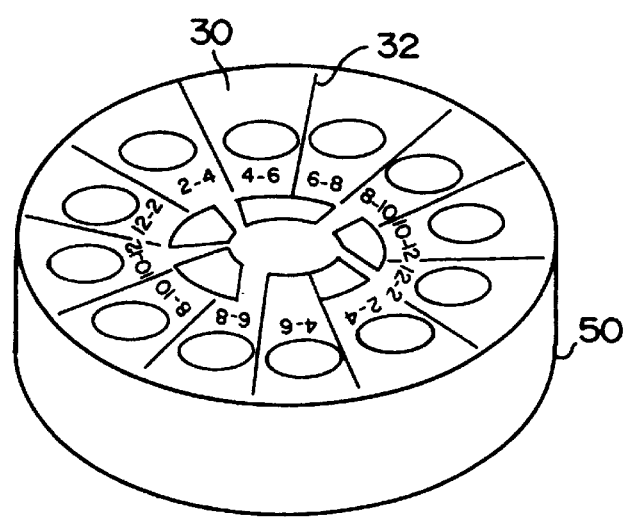
FIG. 6 is a perspective view of an aroma therapy diffuser in accordance with the invention, having a clock face, without the lid or sealing means.

As shown in FIG. 5, heating component 80 includes heating element 84 which is in contact with a heat conducting plug 82. Heating element 84 is held in contact with plug 82 by a retaining ring 88. The user can program timer 60 to activate or deactivate the heating element as desired. When the timer activates the heating elements, heat generated by the heating elements is transferred to the plug, which in turn transfers heat to the receptacle. Heating component 80 also includes an indicator 90, such as a neon bulb, coupled to timer 60. When heating component 80 is activated, the bulb is illuminated, thus indicating the diffuser is in use.

It is preferred that plug 82 be of a material with good heat conductivity properties, such as aluminum. While various heating elements may be used, it is preferred that heating element 84 consist of two sandstone ceramic heating elements wired together, with a resistance of approximately 5 K Ohms. This configuration produces a heat of approximately 650 Celsius, which is below the amount that requires an operating warning under the UL (Underwriters Laboratories) guidelines. It is further preferred that heating component 80 be encased in a thermal plastic material, such as a material known as Delrin®, manufactured by E.I. DuPont, Inc. of Delaware, so as to withstand direct heat generated by heating element 84.

In one embodiment, heating component 80 is removable from surface 52 of housing 50. In another embodiment, heating component 80 is molded into surface 52, the entire surface being made of a thermal plastic material.

As shown in FIG. 2, the diffusing apparatus 100 further includes a seal 20 which seals the receptacles not in close proximity to the heating element so as to minimize evaporation of the aromatic materials that are placed in the receptacles 40. Seal 20 is in the nature of a gasket having a hole 22 and alignment keys 24. Side surfaces 54 of housing 50 have molded keys 56. Seal 20 lies parallel to tray 30, with the perimeter of seal 20 abutting side surfaces 54 of housing 50, and alignment, so that as tray 30 rotates, seal 20 remains stationary. In one embodiment, seal 20 is pressure fit to the housing walls. Hole 22 of the seal is aligned with hole 12 of the lid and heating component 80, thereby allowing the aromas diffused in the receptacle in close proximity to heating component 80 to emanate through hole 22 and hole 12 and into the environment.

Seal 20 may be of any vinyl material that will not be broken down or otherwise corrupted by exposure to the aromatic materials. It is preferred that seal 20 be made of a low density polyethylene, but other materials having similar characteristics may be used.

While timer 60 may be of any type or configuration, such as a microchip, it is preferred that the timer be a mechanical timing device, such as the Intermatic® timer manufactured by Intermatic Incorporated of Spring Grove, Ill., that can be programmed to activate and deactivate an electric device for a 24 hour cycle. Such timing devices are often used to program one's lights to turn on and off, while unattended during a 24 hour time cycle. The timer includes a motor means which engages the rotating means 70, and causes the tray to rotate through the 24 hour cycle. The user can thus select the time periods during which heating component 80 is activated or deactivated for a 24 hour cycle. In one embodiment of the invention, timer 60 is powered by a DC source, such as a battery. In another embodiment, timer 60 is powered by a standard AC source, such as a wall outlet.

In another contemplated embodiment of the invention, as shown in FIG. 7, tray 30 is decorated with the features of a clock face 32. Thus, as tray 30 rotates through the 24 hour cycle of timer 60, the diffusing apparatus functions as a time clock.

In another embodiment of the invention, the rotating means 70 of the timer can be removed thereby disabling the rotation of the tray. A particular receptacle is therefore stationary above heating component 80, and heated as programmed by timer 60.

It is appreciated that other modifications and variations of the apparatus might be made by those skilled in the art without departing from the spirit and scope of the present invention.

What is claimed is:

1. An apparatus for diffusing aromatic materials, comprising:
    a housing;
    a tray having a plurality of receptacles for retaining aromatic materials, disposed along a periphery of the tray, the tray being detachably coupled to the housing;
    a means for heating the aromatic material within one of the plurality of receptacles of the tray, the heating means being disposed within the housing, and having an activated state and a deactivated state;
    a means for rotating the tray disposed within the housing and engageably connected to the tray so as to align said one receptacle with the heating means;
    a lid, disposed above the tray, having an opening through which the aroma released by the aromatic material in said one receptacle emanates when said one receptacle is aligned with the heating means; and
    a means for sealing the plurality of receptacles except for said one receptacle of the tray, so that the aromatic materials do not evaporate.

2. An apparatus as defined in claim 1, further comprising:

a timer for selectively activating the heating means when said one receptacle is aligned with the heating means at a selected time of day.

3. An apparatus as defined in claim 1, wherein:

the plurality of receptacles are removable from the tray.

4. An apparatus as defined in claim 2, wherein:

the means for heating the selected receptacle comprises a heating element coupled to the timer, a heating block for conducting heat from the heating element to the selected receptacle, and a means for retaining the heating element within the heating means, the heating means being encased within a thermal plastic material.

5. An apparatus as defined in claim 4, wherein:

the heating block for conducting heat to the selected receptacle is made of a heat conducting material; and, the means for retaining the heating element includes a retaining ring coupled to the heating element so as to keep the heating element in close proximity to the heating block.

6. An apparatus as defined in claim 1, further comprising:

a means for indicating when the heating means is activated and deactivated.

7. An apparatus as defined in claim 5, wherein:

the means for indicating when the heating means is activated or deactivated comprises a light coupled to the heating means, the light being activated when the heating means is activated, the light being deactivated when the heating means is deactivated.

8. An apparatus as defined in claim 1, wherein:

the means for sealing the plurality of receptacles except for said one receptacle of the tray includes a seal having an opening aligned above the selected receptacle, the seal being coupled to the housing, so that when the tray is engaged by the rotating means, the seal is not engaged.

9. An apparatus as defined in claim 2, wherein:

the tray is decorated with a clock face; and, the rotating means is coupled to the timer so that the tray is rotated through a 24 hour cycle.

* * * * *

UNITED STATES PATENT AND TRADEMARK OFFICE
CERTIFICATE OF CORRECTION

PATENT NO. : 5,805,768
DATED : September 8, 1998
INVENTOR(S) : Schwartz et al.

It is certified that error appears in the above-identified patent and that said Letters Patent is hereby corrected as shown below:

<u>Title page,</u>
Item [21], Appl. No.: , delete "676,823" and insert -- 08/676,823 --.

After "Assistant Examiner—Sam Paik" insert -- [74] Attorney, Agent, or Firm—Blakely, Sokoloff, Taylor & Zafman LLP --.

Signed and Sealed this

Nineteenth Day of March, 2002

Attest:

JAMES E. ROGAN
*Director of the United States Patent and Trademark Office*

*Attesting Officer*